United States Patent [19]

Hughes

[11] 4,201,714
[45] May 6, 1980

[54] STABILIZED CATALYST COMPLEX OF RHODIUM METAL, BIDENTATE LIGAND AND MONODENTATE LIGAND

[75] Inventor: O. Richard Hughes, Chatham, N.J.
[73] Assignee: Celanese Corporation, New York, N.Y.
[21] Appl. No.: 917,245
[22] Filed: Jun. 20, 1978

Related U.S. Application Data

[62] Division of Ser. No. 825,896, Aug. 19, 1977.

[51] Int. Cl.$^2$ .................. C07D 317/00; C07D 323/02
[52] U.S. Cl. .......................... 260/340.9 R; 252/431 P;
260/429 R; 260/439 CY; 260/441
[58] Field of Search ............... 260/429 R, 340.9 R,
260/441, 439 CY; 252/431 P

[56] References Cited
U.S. PATENT DOCUMENTS

| | | | |
|---|---|---|---|
| 3,547,964 | 12/1970 | Olivier | 252/431 P X |
| 3,639,439 | 2/1972 | Dewhirst | 260/429 R |
| 3,652,614 | 3/1972 | Dewhirst et al. | 260/429 R |
| 3,798,241 | 3/1974 | Kagan et al. | 260/429 R X |
| 3,849,480 | 11/1974 | Knowles et al. | 260/429 R |
| 3,939,188 | 2/1976 | McVicker | 252/431 P X |
| 3,949,000 | 4/1976 | Violet | 260/429 R X |
| 3,968,147 | 7/1976 | Solodar | 252/431 P X |
| 4,119,652 | 10/1978 | Knowles et al. | 252/431 P X |
| 4,123,465 | 10/1978 | Valentine | 252/431 P X |
| 4,124,533 | 11/1978 | Knowles et al. | 252/431 P |

*Primary Examiner*—Helen M. S. Sneed
*Attorney, Agent, or Firm*—Kenneth A. Genoni

[57] ABSTRACT

This invention provides a catalyst and process for achieving highly selective straight chain aldehyde formation from alpha-olefins under hydroformylation conditions. The improved hydroformylation results are obtained under mild conditions of temperature and pressure in the presence of a stabilized catalyst complex of rhodium metal, bidentate ligand and monodentate ligand represented by the formula:

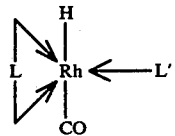

Illustrative of a preferred bidentate ligand is trans 1,2-bis-(diphenylphosphinomethyl)cyclobutane. Illustrative of a preferred monodentate ligand is diphenylethylphosphine. It is an essential feature of the invention process that the monodentate ligand is provided in a molar excess with respect to the rhodium metal in the stabilized catalyst complex.

5 Claims, No Drawings

STABILIZED CATALYST COMPLEX OF RHODIUM METAL, BIDENTATE LIGAND AND MONODENTATE LIGAND

This is a division, of application Ser. No. 825,896, filed Aug. 19, 1977.

BACKGROUND OF THE INVENTION

The hydroformylation reaction is employed on a commercial scale to prepare straight chain and branched chain mixtures of aldehydes and alcohols from olefinically unsaturated hydrocarbons.

The selective production of straight chain aldehydes and alcohols is particularly desirable. Higher oxo alcohols have become important intermediates for synthesis of biodegradable surface-active agents, lubricant esters, and plasticizers. In each of these products straight chain alcohol derivatives are preferred because of biodegradability and other advantageous properties. There is continuing development effort to increase alpha-olefin hydroformylation selectivity to linear paraffinic aldehydes and alcohols.

Cobalt carbonyl is a conventional catalyst employed for hydroformylation reaction, but large quantities of branched chain aldehydes are produced with this catalyst. Rhodium carbonyl complexes containing tertiary phosphine or phosphite ligands [Evans et al, J. Chem. Soc. A, 3133 (1968); Pruett and Smith, J. Org. Chem., 34, 327 (1969)] are useful at low pressures and give higher ratios of straight chain to branched chain products. Similar cobalt carbonyl complexes [Slaugh and Mullineaux, J. Organometal. Chem., 13, 469 (1968)] also give more straight chain product, but produce alcohols as the primary products More recently developed hydroformylation catalysts and processes achieve some selectivity to linear products but still result in a high yield of branched chain aldehyde and alcohol products. Illustrative of recent advances in hydroformylation technology are U.S. Pat. Nos. 3,480,659; 3,488,296; 3,515,757; 3,652,676; 3,681,465; 3,876,672; 3,933,919; 3,939,188; 3,956,177; 3,965,192; 3,981,925; and 3,984,486.

U.S. Pat. No. 3,939,188 describes a hydroformylation process in which propylene is converted to aldehydes in a normal/iso ratio of 2:1 in the presence of a zero valence rhodium catalyst which is stabilized by selected monodentate, bidentate, tridentate or quadradentate ligands:

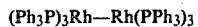

(Ph$_3$P)$_3$Rh—Rh(PPh$_3$)$_3$

U.S. Pat. No. 3,956,177 describes the preparation of a hydroformylation catalyst involving admixture of an alicyclorhodium halide, a reducing agent such as hydrazine, and a phosphorus-containing ligand. In EXAMPLE 1 of the patent reference, hexene-1 is converted to 77.5 percent n-heptaldehyde, 5.6 percent branched C$_7$-aldehydes, and 16.9 percent of internal hexenes.

U.S. Pat. No. 3,965,192 discloses a process for hydroformylation of olefins with a tris(triphenylphosphine) rhodium carbonyl hydride type of catalyst. In EXAMPLE 1 of the patent reference, propylene is converted to aldehydes in a normal/iso ratio of 2:1.

U.S. Pat. No. 3,981,925 discloses a process for hydroformylation of olefins to aldehydes in the presence of a ligand stabilized platinum halide complex in combination with a Group IVA metal halide. The hydroformylation selectivity of the U.S. Pat. No. 3,981,925 process favors formation of straight chain aldehyde, e.g., in Example 1 the mole ratio of 1-octylaldehyde to 2-methylheptaldehyde product from heptene-1 hydroformylation is 9:1. Also produced are 2.7 mole percent of heptene-2 and heptene-3 isomerization products.

There remains further need for improved hydroformylation efficiency and selectivity to straight chain derivatives, and a concomitant reduction in the yield of isomerization, hydrogenation and polymerization products.

Accordingly, it is a main object of the present invention to provide a hydroformylation process for converting alpha-olefins to aldehydes in a normal/iso mole ratio of at least 5:1 and in a conversion efficiency to aldehydes of at least 95 mole percent.

It is a further object of this invention to provide a novel rhodium catalyst system for hydroformylation of alpha-olefins which has improved efficiency and selectivity for linear aldehyde formation.

Other objects and advantages of the present invention shall become apparent from the accompanying description and examples.

DESCRIPTION OF THE INVENTION

One or more objects of the present invention are accomplished by the provision of a process for highly selective hydroformylation of an alpha-olefin to the corresponding terminal aldehyde, which process comprises contacting an alpha-olefin with hydrogen and carbon monoxide at a temperature between about 25° C. and 150° C. and a pressure between about 15 and 3000 psi in the presence of a catalyst consisting essentially of a stabilized complex of rhodium metal, bidentate ligand and monodentate ligand, which catalyst components are provided in a molar ratio of 1 mole of bidentate ligand and between about 1.2–800 moles of monodentate ligand per gram atom of rhodium metal in the hydroformylation medium, and said catalyst complex corresponding to the structural formula:

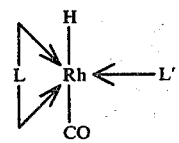

wherein L is a bidentate ligand, and L' is a monodentate ligand having the formula:

Q'R'$_3$ wherein Q' is a group VA element selected from nitrogen, phosphorus and arsenic; R' is an organic radical selected from aliphatic, alicyclic and aromatic groups containing between one and about 20 carbon atoms; and the steric parameter θ of Q'R'$_3$ in the catalyst complex is an apex angle between about 135 and 150 degrees.

The invention process is contemplated for hydroformylation of alpha-olefins containing between about 3 and 30 carbon atoms. The term "alpha-olefin" is meant to include substituted olefinically unsaturated compounds such as styrene, acrolein acetal, allyl alcohol, acrylic acid, vinyl acetate, and the like. The invention process provides particular advantages in the hydroformylation of linear alkene-1 hydrocarbons containing between about 3 and 20 carbon atoms. Illustrative of linear alkene-1 compounds are propene-1, butene-1, pentene-1, hexene-1, heptene-1, decene-1, undecene-1, eicosene-1, and the like.

I. Hydroformylation Catalyst

The novel catalyst for the practice of the present invention hydroformylation process consists essentially of a stabilized complex of (1) rhodium carbonyl hydride; (2) bidentate ligand which is provided in the catalyst system on a 1:1 molar basis with respect to the rhodium metal component of the stabilized catalyst complex; and (3) monodentate ligand which is provided in excess molar quantity with respect to the rhodium metal component of the stabilized catalyst complex.

Bidentate Ligand

The bidentate ligand L is employed in the invention hydroformylation catalyst system in at least a 1:1 molar ratio with respect to the quantity of rhodium metal present in the hydroformylation reaction medium. The bidentate ligand chelates with the rhodium metal:

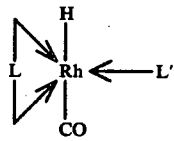

Achievement of a catalyst system which is highly reactive and highly selective for hydroformylation of alpha-olefins to straight chain aldehydes requires that the bidentate contain two group VA elements selected from nitrogen, phosphorus and arsenic, and that the said group VA elements in the bidentate ligand must be structurally positioned relative to each within specific steric constrictions.

One type of bidentate ligand preferred for the preparation of the present invention catalysts are those corresponding to the chemical structure:

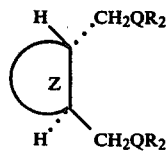

wherein Z is an alicyclic structure, preferably of 3–5 atoms in ring size; Q is a group VA element selected from nitrogen, phosphorus and arsenic; and R is an organic radical selected from aliphatic, alicyclic and aromatic groups containing between one and about 20 carbon atoms. Illustrative of preferred species of this type of bidentate ligand are trans 1,2-bis-(diphenylphosphinomethyl)cyclobutane and trans 1,2-bis-(diphenylphosphinomethyl)-3,5-dioxa-4,4-dimethylcyclopentane.

Another type of bidentate ligand preferred for the preparation of the present invention catalysts are those corresponding to the chemical structure:

wherein Q is a group VA element selected from nitrogen, phosphorus and arsenic; and R is an organic radical containing between one and about 20 carbon atoms, preferably alkyl, aryl, alkoxy-substituted aryl or halogen-substituted aryl. Illustrative of preferred species of this type of bidentate ligand are 1,1'-bis(diphenylphosphino)ferrocene and 1,1'-bis(di-m-fluorophenylphosphino)ferrocene.

Monodentate Ligand

The monodentate ligand is provided in the hydroformylation medium in a molar ratio of between about 1.2–800 moles, preferably between about 5–100 moles, of monodentate ligand per gram atom of rhodium metal.

The preferred monodentate ligands are those which correspond to the formula:

$$Q'R'_3$$

wherein $Q'$ is a group VA element selected from nitrogen, phosphorus and arsenic; and $R'$ is an organic radical containing between one and about 20 carbon atoms which is selected from groups such as alkyl, alkoxy, aryl, aryloxy, and the like. The $R'$ radical can contain heteroatoms such as oxygen, nitrogen and halogen.

It is an important aspect of the present invention hydroformylation catalyst system that the monodentate ligand component is employed in a molar excess, and that the monodentate ligand has an atomic structure with a specific steric configuration in the stabilized catalyst complex, i.e., the steric parameter $\theta$ of the monodentate ligand in the catalyst complex is an apex angle between about 135 and 150 degrees. By the term "steric parameter $\theta$" is meant the apex angle of a cylindrical cone, centered 2.28 Å from the center of the group VA atom $Q'$, which just touches the Van der Waals radii of the outermost atoms of the $R'$ substitutents of a symmetrical $Q'R'_3$ monodentate ligand [C. A. Tolman, J. Amer. Chem., Soc., 92, 2953 (1970); Ibid, 92, 2956 (1970); and Ibid, 96, 53 (1974)].

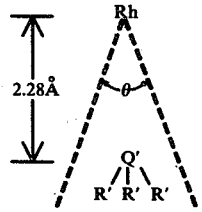

The steric parameter $\theta$ apex angle of an unsymmetrical ligand (e.g., $Q'R^1R^2R^3$, where $R^1$, $R^2$ and $R^3$ are different hydrocarbyl groups) can be estimated from a knowledge of the cone angles of the corresponding symmetrical ligands $Q'(R^1)_3$, $Q'(R^2)_3$ and $Q'(R^3)_3$, on the basis of the formula:

$$\theta(Q'R^1R^2R^3) = \frac{2}{3}\left[\frac{\theta[Q'(R^1)_3]}{2} + \frac{\theta[Q'(R^2)_3]}{2} + \frac{\theta[Q'(R^3)_3]}{2}\right]$$

Illustrative of monodentate ligand chemical structures having a steric parameter $\theta$ apex angle between 135 and 150 degrees are diethylphenylphosphine, diphenylmethylphosphine, diphenylethylphosphine, tris(trifluoromethyl)phosphine, tri(o-tolyl)phosphite, tri(isobutyl)phosphine, tri(isobutyl)amine, tri(isobutyl)arsine, triphenylamine, triphenylphosphine, tri(p-tolyl)phosphine, tri(m-fluorophenyl)phosphine, tri(o-isopropylphenyl)phosphite, and isopropyldiphenylphosphine. It is convenient to employ diphenylethylphosphine as the monodentate ligand because it is readily available, and it has excellent solubility characteristics when employed in molar excess in the hydroformylation reaction medium.

Catalyst Preparation

The present invention catalysts, which correspond to the formula:

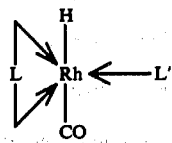

wherein L and L' are as defined hereinabove, can be prepared in situ in the hydroformylation reaction zone or, alternatively, can be prepared ex-situ and subsequently introduced into the reaction zone with the appropriate hydroformylation reactants. The most preferred catalysts are prepared by admixing one mole of suitable rhodium source with one mole of bidentate ligand L and between about 5–100 moles of monodentate ligand L'.

The amount of processing required for conversion of the rhodium metal depends on the nature of the initial rhodium source. Hence, if the rhodium in the starting material source is a salt in which rhodium is the cation moiety (e.g., a $Rh^{+3}$ valence state), at some stage in the catalyst preparation or in the hydroformylation process the rhodium metal must be reduced to the $Rh^{+1}$ valence state. The reduction is normally accomplished with hydrogen, or other reducing agents. When the rhodium source compound contains halogen, then a halide scavenger is employed in connection with the rhodium valence state reduction so as to eliminate the hydrogen halide as it is generated during the reduction step. This can be achieved by contact with $H_2/CO$ in the hydroformylation process, or alternatively by employment of an equivalent source of hydrogen such as hydride (e.g., sodium borohydride).

In a preferred method of catalyst preparation, the rhodium source compound (e.g., a rhodium salt of a mineral acid or a carboxylic acid) is converted to a carbonyl derivative in a first step, followed by subsequent reaction of the rhodium carbonyl derivative with the bidentate and monodentate ligands. If the primary rhodium source compound is already a carbonyl-containing compound, then the initial carbonylation step can be eliminated.

Suitable rhodium sources which do not already comprise a carbonyl moiety in the molecule include the simple salts such as the halides (especially rhodium trichloride trihydrate), rhodium sulfate, rhodium nitrate, and rhodium carboxylates including the rhodium salts of simple carboxylic acids and dicarboxylic acids. Rhodium sources already containing carbonyl moiety in the molecule include $(PPh_3)_3Rh(CO)H$, $(PPh_3)_2Rh(CO)Cl$, $Rh_6(CO)_{16}$ and rhodium carbonyl chloride dimer (i.e., $[Rh(CO_2)Cl]_2$. The material known in the trade as "rhodium on carbon," which comprises a mixture of rhodium oxides of a rather complex nature on a carbon support, can also be employed. hydridocarbonyltris(triphenylphosphine) rhodium (I) is a highly preferred rhodium source for catalyst preparations.

The various methods of preparing the present invention ligand stabilized rhodium catalysts can be summarized as follows:

(1) When the rhodium is initially in a non-carbonyl form, the rhodium is converted to a carbonyl derivative by reaction with carbon monoxide. Typical carbonylation procedures are described in "Inorganic Synthesis," Vol. 8, 211 (1966).

The rhodium carbonyl compound is then combined with the bidentate ligand and monodentate ligand components of the catalyst system.

If hydrogen halide is generated during the catalyst preparation, a base is added as a halide scavenger. Alkaline borohydride is a versatile reagent for rhodium valence state reduction from $Rh^{+3}$ to $Rh^{+1}$, and for concomitant halide scavenging.

(2) When rhodium is initially available in the form of a carbonyl derivative, the rhodium carbonyl compound is reacted directly with the bidentate and monodentate ligands to form the ligand stabilized rhodium catalyst. When the rhodium carbonyl derivative is a compound such as rhodium carbonyl chloride dimer, the interaction with the bidentate and monodentate ligands is conducted in the presence of (1) a hydrogen chloride scavenger such as pyridine or sodium hydroxide, and (2) a hydride source such as hydrogen or a borohydride.

(3) Another alternative which is a covenient laboratory procedure is to form the bidentate rhodium carbonyl hydride by displacing triarylphosphine ligands from hydridocarbonyltris(triphenylphosphine) rhodium (I) with bidentate ligand:

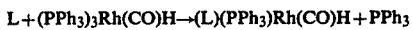

This produces a complex with L as the bidentate ligand and $PPh_3$ as the monodentate ligand. Other monodentate ligands can be introduced by displacing the remaining $PPh_3$ ligand:

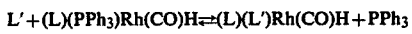

In order to shift the equilibrium to increase the displacement of $PPh_3$, it is usually required to incorporate in the reaction medium an excess of L' ligand, e.g., 5–20 moles of L' per mole of rhodium metal in the complex.

The catalyst preparation procedures described above are all conducted in the liquid phase and preferably in the presence of an inert solvent such as benzene or toluene. Suitable reaction temperatures are in the range between about 25° C. and 100° C.

II. Hydroformylation Conditions

As a general procedure, the catalyst system is first formed in a deoxygenated solvent medium in a hydroformylation reaction zone in a manner as described above. Excess monodentate ligand can perform as the solvent medium. The hydroformylation zone is pressured with hydrogen and carbon monoxide and heated to a selected reaction temperature. Alpha-olefin feed is then charged to the hydroformylation zone, and the reaction is conducted until the desired conversion yield and efficiency have been attained.

It is preferred that the temperature of the hydroformylation reaction be maintained in the range between about 25° C. and 150° C. For most of the alpha-olefin hydroformylation reactions, a reaction temperature between about 50° C. and 110° C. and a reaction time between about 0.1 and 3 hours are particularly preferred.

The pressure in the hydroformylation reaction zone is not critical, and can vary over a wide range between about 15–3000 psi. Preferred pressures are those in the range between about 50–500 psi.

The ratio of hydrogen to carbon monoxide can vary broadly over a mole ratio range between about 30:1 and 1:30. The average mole ratio will vary between about 10:1 and 1:10. The quantity of hydrogen/carbon monoxide charged should be at least sufficient to satisfy the stoichiometric requirements of the alpha-olefin hydroformylation system.

Although it is not essential, an inert solvent can be employed as a hydroformylation reaction medium diluent. A variety of solvents can be used including ketones such as acetone, methyl ethyl ketone, methyl isobutyl ketone, acetophenone, and cyclohexanone; aromatics such as benzene, toluene and xylenes; halogenated aromatics including orthodichlorobenzene; ethers such as tetrahydrofuran, dimethoxyethane and dioxane; halogenated paraffins including methylene chloride; paraffinic hydrocarbons such as heptane; and the like.

It is an important aspect of the present invention that the hydroformylation process is conducted in the presence of excess monodentate ligand:

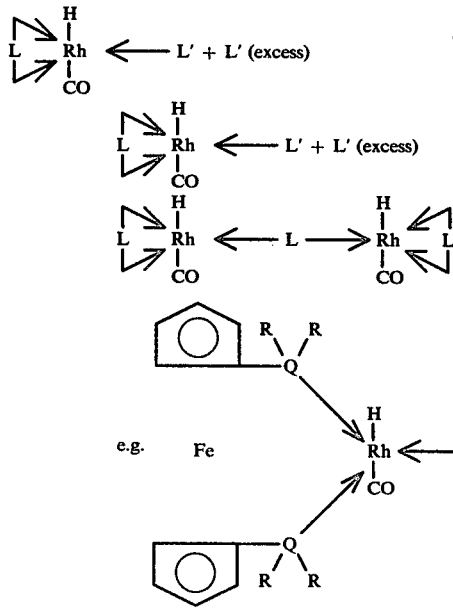

The effect of the excess monodentate ligand is to shift the reaction equilibrium to the right:

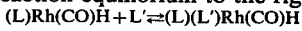

(L)Rh(CO)H + L' ⇌ (L)(L')Rh(CO)H

It is essential that the monodentate L' ligand component of the ligand stabilized catalyst has a steric parameter $\theta$ apex angle in the range between about 135 and 150 degrees, in order to achieve optimum advantages in the practice of the invention process, i.e., highly selective and efficient conversion of alpha-olefin to alkanal-1.

If in the practice of the present invention process a molar excess of monodentate ligand L' is not employed, then the selectivity efficiency of alpha-olefin to alkanal-1 is lowered. Hence, under comparable process conditions except for the presence of or lack of a molar excess of monodentate ligand L', hydroformylation of hexene-1 yields aldehydes in a normal/iso ratio of about 6:1 in the presence of excess monodentate (e.g., 5/1, L'/Rh), and yields a normal/iso ratio of about 3:1 in the absence of excess monodentate ligand L'.

The excess monodentate ligand L' appears to have the beneficial effect of stabilizing the catalyst and maintaining it in the form of a complex with high alpha-olefin to alkanal-1 selectivity under hydroformylation conditions. Elevated temperatures can cause dissociation of the complex, and presumably elevated carbon monoxide pressure can cause a displacement of phosphine ligand:

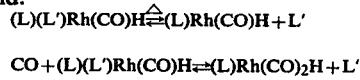

(L)(L')Rh(CO)H ⇌ (L)Rh(CO)H + L'

CO + (L)(L')Rh(CO)H ⇌ (L)Rh(CO)$_2$H + L'

In either of the reaction sequences illustrated above, it appears that the function of excess monodentate L' is to shift the equilibrium to the left in favor of the highly selective form of the hydroformylation catalyst complex.

It is believed that the selectivity efficiency of the various related hydroformylation catalysts is determined by steric nature of the respective ligand stabilized rhodium structures. On an empirical basis it appears that the following steric configurations are equivalent for highly selective conversion of alkene-1 to alkanal-1 under hydroformylation conditions:

(a)

(b)

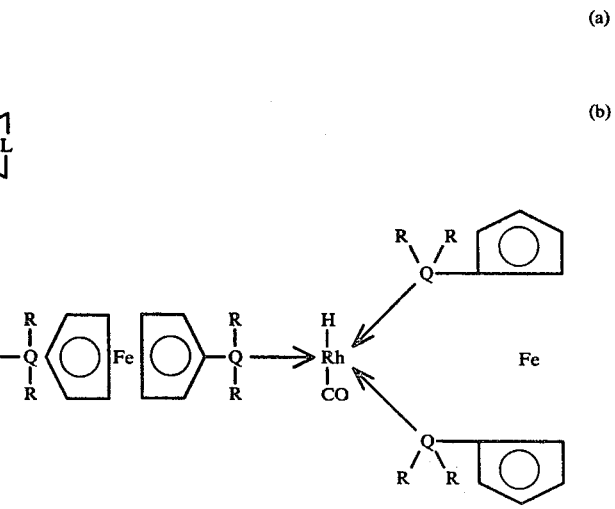

wherein L, L', Q and R are substituents as previously defined.

Rhodium catalysts which demonstrate lower selectivity of alkene-1 to alkanal-1 conversion appear to have the following steric configurations.

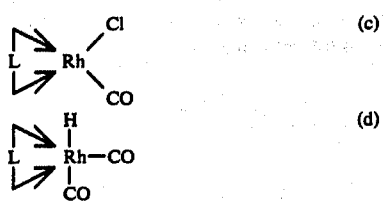

The catalyst configurations (a) and (b) are described above as being equivalent for highly selective and efficient hydroformylation of alkene-1 to alkanal-1. As it is apparent from a comparison of catalysts (a) and (b), the catalyst structure (a) contains one mole of bidentate ligand L per mole of rhodium, and catalyst structure (b) contains 1.5 moles of bidentate ligand L per mole of rhodium. For reasons of economy, it is advantageous to employ catalyst (a) rather than catalyst (b) for hydroformylation reactions. Monodentate ligand L' is relatively inexpensive and readily available in comparison with bidentate ligand L.

A further economic advantage of catalyst (a) is the ability of the excess monodentate ligand L' to scavenge the oxygen present in a hydroformylation reaction system, which thereby protects the integrity of the stabilized rhodium catalyst in general, and the expensive bidentate ligand L in particular.

Another practical advantage derives from the use of catalyst (a) defined above in comparison with a prior art rhodium catalyst composition of the following type:

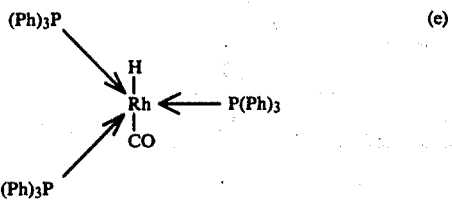

To achieve highly selective hydroformylation of alkene-1 to alkanal-1, U.S. Pat. No. 3,527,809 proposes the use of a catalyst (e) type of stabilized rhodium structure in the presence of an excess of monodentate ligand (e.g., 2–100 moles of ligand per mole of rhodium metal). In actual practice on a commercial scale, a large excess of triarylphosphine (e.g., >100:1) is required to promote catalyst selectivity for alkanal-1 formation and to function as a solvent medium. Such a hydroformylation system has the disadvantage of high triarylphosphine ligand cost. Also, a high content of triarylphosphine in the hydroformylation medium (e.g., greater than 30 weight percent) renders the medium susceptible to partial solidification if a temperature sufficiently above room temperature is not maintained, i.e., a temperature of at least about 80° C.

The present invention hydroformylation process has the advantage of highly selective alkanal-1 formation in the presence of a relatively minor excess of monodentate ligand L'. The present invention hydroformylation process has the further advantage of having a reaction medium which is liquid at room temperature or at lower temperatures.

The following examples are illustrative of specific embodiments of the present invention process. As it is apparent to those skilled in the art, in the light of the foregoing disclosure numerous modifications are possible in the practice of the invention process without departing from the scope or concept thereof.

In the following examples, the ligand abbreviations correspond to the following chemical nomenclature:

| | |
|---|---|
| BDMCB | trans 1,2-bis(diphenylphosphinomethyl)cyclobutane |
| DIOP | trans 1,2-bis(diphenylphosphinomethyl)-3,5-dioxa-4,4-dimethylcyclopentane |
| FL | 1,1'-bis(diphenylphosphino)ferrocene |
| TNOP | tri(n-octyl)phosphine |
| BDPP | 1,3-bis(diphenylphosphino)propane |
| BDPB | 1,4-bis(diphenylphosphino)butane |
| CAMPHOS | 1,3-bis(diphenylphosphinomethyl)-1,2,2-trimethylcyclopentane |
| TIBP | tri(isobutyl)phosphine |
| TPP | triphenylphosphine |
| PCyPh$_2$ | cyclohexyldiphenylphosphine |
| TAMP | tri(diethylaminomethyl)phosphine |

EXAMPLE I

This Example illustrates a general procedure for catalyst preparation in accordance with the present invention.

(TPP)$_3$Rh(CO)H was freshly prepared from (TPP)$_2$Rh(CO)Cl in the presence of excess TPP according to the procedure of Evans et al, J. Chem. Soc., 2660 (1968).

Under a nitrogen atmosphere, 0.185 gram (2.02 mM) of (TPP)$_3$Rh(CO)H in 76.4 grams of toluene and 4 grams of benzene were admixed with the appropriate quantities of bidentate ligand L and monodentate ligand L' to form a solution of a stabilized catalyst complex as previously defined herein:

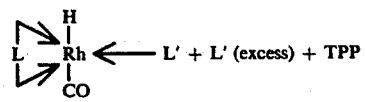

The stabilized catalyst complex structure was confirmed by NMR examination.

EXAMPLE II

This Example illustrates a general procedure for hydroformylation of alkene-1 in accordance with the present invention.

A catalyst solution prepared in the manner of EXAMPLE I was charged to a 300 milliliter Magnadrive stirred autoclave. The autoclave was purged with H$_2$/CO (1:1) gas.

A 13.4 gram quantity of hexene-1 in 10 milliliters of toluene was charged to a reservoir unit that was connected to the autoclave as a feed source. Both the autoclave and reservoir were pressured to the desired reaction pressure (e.g., 100 psig) with H$_2$/CO (1:1), and the autoclave was heated to hydroformylation reaction temperature (e.g., 100° C.–110° C.).

The hydroformylation reaction was commenced by transferring the hexene-1 feed solution from the reservoir to the autoclave reactor.

As in the case of most of the Examples described herein, after about a 20-minute reaction time the hexene-1 was converted 90–100 percent to a product mixture containing a major quantity of heptanal.

The composition of the product mixture was determined by gas chromatography to consist essentially of heptanal, 2-methylhexanal, hexene-2, hexene-3 and hexane.

EXAMPLE III

In the manner of EXAMPLE II, hydroformylation of hexene-1 was conducted employing different combinations and proportions of rhodium metal, bidentate ligand L and monodentate ligand L', and approximately the same conditions of temperature (100° C.) and pressure (100 psig). A 1:1 mixture of $H_2$/CO was employed, and the hexene-1 was substantially converted to a product mixture after about 20 minutes.

The hexene-1 hydroformylation results are reported in TABLE A, with the analysis of the respective product mixtures as determined by gas chromatography.

The steric parameter $\theta$ is indicated for each of the stabilized catalyst complex structures. It is to be noted that the $\theta$ value in the case of the catalysts in Run Numbers 3–8 is within the range of 135–150 degrees as provided by the present invention.

The hydroformylation data obtained are listed in TABLE B, with the composition of the respective product mixtures as determined by gas chromatography.

TABLE B

| Run No. | L | L/Rh | L' | L'/Rh | Hexane | Hexene-2 and Hexene-3 | 2-Methyl-hexanal | Heptanal | Aldehyde Normal/Iso Ratio |
|---|---|---|---|---|---|---|---|---|---|
| 11 | FL | 1 | — | — | 1 | 21 | 24 | 54 | 2 |
| 12 | " | 1 | PEtPh$_2$ | 10 | 0.3 | 3 | 20 | 77 | 4 |
| 13 | " | 1 | PCyPh$_2$ | 10 | 0.4 | 5 | 20 | 75 | 4 |
| 14 | " | 1 | TIBP | 2 | 0.2 | 18 | 19 | 64 | 3 |
| 15 | " | 1 | TAMP | 100 | 0.6 | 1.4 | 16 | 82 | 5 |
| 16 | " | 1.5 | — | — | 1 | 0.5 | 16 | 83 | 5 |

EXAMPLE V

In the manner of EXAMPLES II–IV, hexene-1 was hydroformylated in the presence of trans 1,2-bis(diphenylphosphinomethyl)-3,5-dioxa-4,4-dimethylcyclopentane (DIOP) as a bidentate ligand alone with rhodium metal, and in combination with monodentate ligand and rhodium metal.

The hydroformylation data obtained are listed in TABLE C, with the composition of the respective product mixtures as determined by gas chromatography.

The results demonstrate that a present invention catalyst composition employing an excess of monodentate ligand provides selectivity and efficiency of alkene-1 conversion to alkanal-1 (Run Numbers 21–22) compara-

TABLE A

| Run No. | L* | L' | L'/Rh | Hexane | Hexene-2 and Hexene-3 | 2-Methyl-hexanal | Heptanal | Aldehyde Normal/Iso Ratio | Steric Parameter $\theta$ Degrees |
|---|---|---|---|---|---|---|---|---|---|
| 1 | BDMCB | PMe$_2$Ph | 5 | 0.9 | 0.5 | 22 | 76 | 3.5 | 122° |
| 2 | " | TNOP | 10 | 0.4 | 0.4 | 17 | 82 | 4.8 | 132° |
| 3 | " | PEtPh$_2$ | 5 | — | 2 | 14 | 84 | 6 | 140° |
| 4 | " | PEtPh$_2$ | 5 | 0.4 | 1 | 13 | 85 | 6.5 | 140° |
| 5 | " | TIBP | 2 | 0.5 | 6 | 13 | 80 | 6.2 | 143° |
| 6 | " | TIBP | 10 | 0.4 | 2 | 13 | 85 | 6.5 | 143° |
| 7 | " | TPP | 10 | 0.5 | 4 | 14 | 82 | 5.9 | 145° |
| 8 | " | TPP | 50 | 0.5 | 4 | 18 | 78 | 4.3 | 145° |
| 9 | " | PCyPh$_2$ | 2 | 0.2 | 9 | 16 | 75 | 4.7 | 153° |
| 10 | " | PCyPh$_2$ | 10 | 0.5 | 9 | 21 | 69 | 3.3 | 153° |

*L/Rh, 1:1

EXAMPLE IV ble to that obtained with an excess of bidentate ligand (Run Numbers 17–20).

TABLE C

| Run No. | L | L/Rh | L' | L'/Rh | Hexane | Hexene-2 and Hexene-3 | 2-Methyl-hexanal | Heptanal | Aldehyde Normal/Iso Ratio |
|---|---|---|---|---|---|---|---|---|---|
| 17 | DIOP | 1 | — | — | 0.4 | 33 | 20 | 47 | 2 |
| 18 | " | 1.5 | — | — | 0.1 | 17 | 19 | 64 | 3 |
| 19 | " | 2 | — | — | 0.4 | 0.8 | 14 | 85 | 6 |
| 20 | " | 2 | — | — | 0.1 | 0.2 | 17 | 83 | 5 |
| 21 | " | 1 | PEtPh$_2$ | 0.5 | — | 14 | 20 | 66 | 3 |
| 22 | " | 1 | " | 5 | 0.4 | 3 | 18 | 79 | 4 |

In the manner of EXAMPLES II–III, hydroformylation of hexene-1 was accomplished in the presence of trans 1,1'-bis(diphenylphosphino)ferrocene as a bidentate ligand alone with rhodium metal, and in combination with various monodentate ligands and rhodium metal.

EXAMPLE VI

This Example illustrates the less desirable results which are obtained when hydroformylation of hexene-1 is conducted in the presence of a ligand stabilized rhodium catalyst complex not in accordance with the present invention. p In the manner of EXAMPLES II–V, hexene-1 was hydroformylated in the presence of individual monodentate and bidentate ligands in various proportions in combination with rhodium metal.

The hydroformylation data obtained are listed in TABLE D, with the composition of the respective product mixtures as determined by gas chromatography.

In TABLE D, it is noted that the best selectivity and efficiency of hexene-1 conversion was obtained when a molar ratio of triphenylphosphine to rhodium metal of 227:1 was employed.

TABLE D

| Run No. | L | L/Rh | L' | L'/Rh | Hexane | Hexene-2 and Hexene-3 | 2-Methyl-hexanal | Heptanal | Aldehyde Normal/Iso Ratio |
|---|---|---|---|---|---|---|---|---|---|
| | | | | | | Product Efficiency, Mole Percent | | | |
| 23 | — | — | TPP | 6 | 0.4 | 16 | 22 | 62 | 3 |
| 24 | — | — | TPP | 227 | 0.2 | 5 | 13 | 82 | 6 |
| 25 | — | — | PEtPh$_2$ | 5 | 0.2 | 14 | 20 | 66 | 3 |
| 26 | — | — | PEtPh$_2$ | 20 | 0 | 4 | 23 | 73 | 3 |
| 27 | — | — | TIBP | 1 | 0.3 | 16 | 24 | 59 | 2 |
| 28 | BDPP | 1.5 | — | — | 0.5 | 18 | 25 | 57 | 2 |
| 29 | BDPP | 5 | — | — | 0.5 | .6 | 59 | 40 | .7 |
| 30 | BDPB | 1.5 | — | — | 0.4 | 4 | 27 | 69 | 3 |
| 31 | CAMPHOS | 3 | — | — | 0.4 | 46 | 18 | 35 | 2 |

What is claimed is:

1. A stabilized catalyst complex of rhodium metal, bidentate ligand and monodentate ligand, said catalyst complex corresponding to the structural formula:

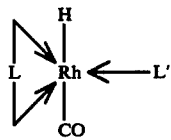

wherein L is a bidentate ligand having the formula:

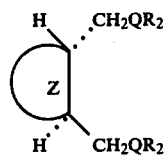

where Z is an alicyclic structure; Q is a group VA element selected from nitrogen, phosphorus and arsenic; and R is an organic radical selected from aliphatic, alicyclic and aromatic groups containing between one and about 20 carbon atoms; and wherein L' is a monodentate ligand having the formula:

$$Q'R'_3$$

where Q' is a group VA element selected from nitrogen, phosphorus and arsenic; R' is an organic radical selected from aliphatic, alicyclic and aromatic groups containing between one and about 20 carbon atoms; and the steric parameter $\theta$ of Q'R'$_3$ in the catalyst complex is an apex angle between about 135 and 150 degrees.

2. A stabilized catalyst complex in accordance with claim 1 wherein L is trans 1,2-bis(diphenylphosphinomethyl)cyclobutane.

3. A stabilized catalyst complex in accordance with claim 1 wherein L is trans 1,2-bis(diphenylphosphinomethyl)-3,5-dioxa-4,4-dimethylcyclopentane.

4. A stabilized catalyst complex in accordance with claim 1 wherein L' is diphenylethylphosphine.

5. A stabilized catalyst complex in accordance with claim 1 wherein L' is triphenylphosphine.

* * * * *